United States Patent [19]

Galabov et al.

[11] Patent Number: 4,499,093

[45] Date of Patent: Feb. 12, 1985

[54] INTERFERON INDUCTION METHOD

[75] Inventors: Angel S. Galabov; Margarita H. Mastikova, both of Sofia, Bulgaria

[73] Assignee: Dso "Pharmachim", Sofia, Bulgaria

[21] Appl. No.: 458,262

[22] Filed: Jan. 17, 1983

[30] Foreign Application Priority Data

Jan. 19, 1982 [BG] Bulgaria .................................. 55032

[51] Int. Cl.³ .......................................... A61K 31/505
[52] U.S. Cl. .................................................. 514/258
[58] Field of Search ........................................ 424/251

[56] References Cited

PUBLICATIONS

Merck Index, 8th Edition (1968), p. 392.

Primary Examiner—Leonard Schenkman
Assistant Examiner—Joseph A. Lipovsky
Attorney, Agent, or Firm—Karl F. Ross; Herbert Dubno

[57] ABSTRACT

Interferon is produced in vivo or in vitro by administration of dipyridamole as interferon inducer to cellular material. Interferon may be induced in warm blooded animals by administration of dipyridamole orally in single doses of 1.0 to 100 mg/kg, intraperitoneally in single doses of 0.1 to 16.7 mg/kg and intravenously in an amount of 0.01 to 50 mg/kg.

2 Claims, 2 Drawing Figures

INTERFERON INDUCTION METHOD

This invention is related to an interferon induction method and its application in medicine and veterinary surgery, especially for the prophylaxy and treatment of some diseases (viral infections, etc) and for the manufacture of interferon.

There are now methods for interferon induction where use is made of viruses, flycolipids of enterobacteria and other bacterial endotoxins, double-standed phage RNA (double-stranded RNA of phage f2 of *Escherichia coli,* statolon), synthetic double-standed polyribonucleotides (poly I:C, poly G:C, poly A:U, etc), some polyanions (pyran, polyacrylic, polymethacrylic, polyacetalcarboxyl acids, etc.) and some synthetic low molecular weight substances: tilorone-hydrochloride and other fluorene products; cationic dyestuffs (toluidine blue, methylene blue, trypaflavine, acridine orange, mepacrine dihydrochloride, acranil-dihydrochloride, etc.); N,N-dioctadecyl-N,N'-bis(2-hydroxyethyl)-propanediamine; 4(3-dimethylaminopropylamino)-1,3-dimethyl-1H-pyrazolo-[3,4-b] quinoline-dihydrochloride, its 7-methyl derivative and other pyrazolo [3,4-b] quinolines; bis-ω-piperidinylacetylbenzofuran-hydrochloride; S,2-aminoethylisothiouronium and related compounds; 2-amino-5-bromo-6-methyl-4-pyrimidinol and other related compounds; 3-(5,7-dimethyl-4-oxo-2-hydroxy-6,8-decadienyl)-glutarimide (9-methylstreptimidone) and other related substances.

It is well-known that the interferon inducers find application: (a) as means of production of exogeneous interferon (Sendai virus and Newcastle disease virus-)—a substance of protein nature applied as a technique for the prophylaxy and treatment of viral infections and in some oncologic diseases, etc.; (b) as antiviral means: double-stranded RNA of phage f2 of *E. coli,* poly G:C, gossipol (polyphenol isolated from cotton oil), and others.

Only the preparation of the double-stranded RNA of phage f2 of *E. coli* and gossipol have so far found clinical application amongst the known interferon inducers (both natural substances and synthetic products), both applied only locally (ointments and other local forms) in viral infections caused by herpes viruses. There is evidence of limited studies of volunteers for the specific effect of propandiamine applied locally in rhinoviral infections, there are controversial data about the effectiveness of some synthetic polyribonucleotides (poly I:C, poly G:C, poly A:U) in local application mainly in herpes keratoconjuctivites. The latter, and especially poly I:C prove to be toxic internally. Experimentally (in vivo), the highly active low molecular interferon inducer, tilorone-hydrochloride also proved toxic and unsuitable for clinical application. The application of inactivated viruses as inducers for viral infection prophylaxis lacks perspective as the introduction of large virus doses is required for stimulating the interferon production and this is far from being unharmful. The application of live vaccine viral strains also has many disadvantages: short-time antiviral activity, need for frequent introduction in the organism of a whole series of antigenously different infectious viral strains, possible reduction of body resistance to infectious agents, unfavorable effect on antibody formation. It becomes clear that at present there is no efficient endogenous interferon inducer for internal application which would greatly increase the indications for using this basic approach for stimulation of the non-specific organism resistance in viral infections.

As production inducers of exogenous interferon only two viruses have found application so far: Sendai virus and the Newcastle Disease virus. But the application of synthetic inducers would offer potential benefits, especially for the reduction of some technological procedures for the elimination of the infectious inducer virus.

It is the object of this invention to provide a method for interferon induction guaranteeing the production of high titres for the interferon in the organism and interferon expressed production in cells cultivated in vitro.

This problem is solved by applying the compound:

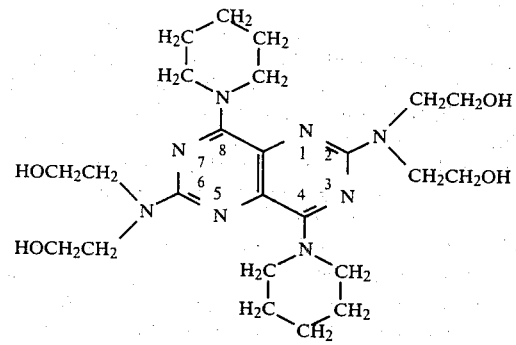

2,6-bis (diethanolamino)-4,8-dipiperidinopyramido [5,4-d]pyrimidine (Dipyridamole)

The dipyridamole compound is known and has been applied as a medicinal preparation: coronary vasodilatator and antiaggregant. Its antiviral effect in in vitro testing (in cellular cultures) towards some DNA and RNA-containing viruses is also known.

The interferon inducing activity of dipyridamole has been established in vitro in lymphoid cell cultures (explanted, cell lines) and non-lymphoid cells (primary cultures, cellular lines and strains), human, mice, etc., and in in vivo in white mice and humans.

Mainly two methods are employed for characterizing the dipyridamole interferon-inducing activity in vitro: in lymphoid cell suspension culture—explanted mouse peritoneal leucocytes prepared according to Lackvi et al. ($2.5 \times 10^6$ cells in 1 ml medium—medium 199 plus 10% inactivated calf serum). Dipyridamole is added immediately after the preparation of the culture; interferon titration samples are taken after cell incubation for 20 hours at 37° C. In monolayer cellular cultures (L-cells, mouse embryonal fibroblasts, human diploid embryonal pulmonary fibroblasts), the interferon titre is measured and the antiviral resistance is simultaneously determined. The cells (preferably cultivated for a longer time—96 hours) are treated with dipyridamole for 4 hours at 37° C. (in medium 199 plus 10% inactivated calf serum), followed by double washing and the addition of fresh medium (199 plus 2% inactivated calf serum), not containing dipyridamole. Incubation of the cultures is carried out for 24 hours at 37° C.; The culture medium after determining its cytotoxicity microscopically is collected for the interferon titre measurement. The cells are rinsed in Hanks' saline solution and inoculated by 100 $TCID_{50}$ virus of the vesicular stomatite (Indiana strain). The cytopathic effect and the infectious virus yield are specified the basis of which the state of the antiviral resistancy is determined.

For the the determination of the interferon-inducing activity in vivo, the dipyridamole is applied once on female white mice weighing 20–25 g using different methods of administration: intravenous, introperitoneal or oral administration. Serum samples for measuring the interferon titre are taken on the 6th, 12th, 24th, 48th, 72nd and 96th hour (mixed serum sample of minimum 8 animals). The control consists of a group of animals not treated with dipyridamole. The acute compound toxicity for the different methods of administration ($LD_{50}$) is determined in advance.

The interferon titre in the serum is determined on human volunteers in advance (immediately before the dipyridamole administration). Serum samples are taken on the 24th and 48th hour after a single oral dipyridamole 100 mg application for the determination of the interferon titre (individually).

The interferon titre is is determined as follows: by the plaque-inhibition method in L-cells or in human embryonal diploid fibroblasts using the vesicular stomatite virus (Indiana strain) by a detector virus; by the cytopathic effect inhibition method of the same virus (using human embryonal diploid fibroblasts). It is expressed in IU/ml by comparing the reference preparations of mouse or human interferon.

The interferon identification induced by dipyridamole is made by a series of tests: contact sample for lack of virocidic effect, antiviral specificity lack test, test for species specificity, resistance test at pH 2.0, heat resistance test (30–60 min at 56° C., 65° C. and 75° C.), trypsin sensitivity, to ribonuclease, desoxyribonuclease, interferon neutralization test using anti-interferon serum and 1,2 and 4 IU of the interferon tested and reference preparations.

The dipyridamole antiviral effect as interferon inducer in vivo has been proved in experimental infections: with Semliki virus, *Herpes simplex* type 1 virus and influenza virus A in white mice (10–12 g). In the first two infection models (Semliki, *Herpes simplex* 1) 10 $LD_{50}$ viruses are administered. The dipyridamole is administered once inttraperitoneally or orally (24 hours before, 24 hours after or 72 hours after the viral inoculation). The dynamics of the mortality cumulative percentage is determined (alpha-viral or herpes encephalitis) in comparison with the controls (placebo).

Dipyridamole manifests clear interferon-inducing activity in lymphoid cells. In mouse peritoneal leucocytes the maximum interferon titres induced under the effect of the optimum interferon-inducing concentration (100 µM) exceed 256 IU/ml.

Dipyridamole also induces interferon production in non-lymphoid human or mouse cellular cultures (human embryonal diploid fibroblasts, mouse embryonal fibroblasts, L-cells) and in L-cells the induced titres exceed 128 IU/ml. The data about the interferon-inducing activity of the compound in vitro are illustrated in Table 1 on the basis of the main qualitative parameters: minimum interferon-inducing concentration (MinINF-IC), optimum interferon-inducing concentration (OptINF-IC) and maximum interferon titre induced by OptINF-IC. The satisfactory selectivity of this dipyridamole effect is worth noticing: the ratio between the maximum cell tolerable concentration and MinINF-IC for mouse peritoneal leucocytes is over 100; for L-cells it is over 30 and for human diploid fibroblasts over 30.

Dipyridamole has strongly marked interferon-inducing activity in vivo. In white mice this compound is especially efficacious in oral administration in single doses in the range 1.12–100 mg/kg. Marked levels of the serum interferon (128–256 IU/ml) are detected as early as on the 12th hour. Maximum titres are detected on the 24–48 hour: 4096–8192 IU/ml. Regardless of whether the interferon content reduction is determined after the 72nd hour, marked interferon levels in the blood are established as late as on the 120th hour.

The compound also induces interferon production in intraperitoneal and intravenous administration. In these cases the effective doses amount to 0.1–16.7 mg/kg or more, and 0.01–50 mg/kg, respectively, but the maximum titres achieved are relatively lower: 256 and 128 IU/ml for the optimum doses of 16.7 and 0.1 mg/kg, respectively.

The dipyridamole interferon-inducing ability is marked by well-expressed selectivity. In oral administration, the single (acute) $LD_{50}$ of the compound is 2150 mg/kg, i.e. the selective index is in the value range of 21.5–689. In intravenous administration, the single $LD_{50}$ is 150 mg/kg, i.e. the selectivity index in that case also reaches quite high values—up to 1500.

Dipyridamole, taken by human volunteers orally in single 10 mg doses (1–2 mg/kg) stimulated marked interferon production in 80% of the treated subjects. Over 200-time increase of the average geometrical titres of interferon in the blood is recorded 24–48 hours in comparison with the initial level: from $5.2 \pm 1.7$ IU/ml initial level, to $1069.0 \pm 479.7$ IU/ml.

The interferon, induced in cellular cultures and contained in the blood serum after dipyridamole administration is identified by means of complex physicochemical and biological tests and by means of immunological test for neutralization by anti-interferon sera (globulins) like IFN-α and IFN-β.

Applied in single doses corresponding to the interferon-inducing ones, dipyridamole manifests marked antiviral activity in viral infections in vivo. In experimental viral infections in test animals (white mice) with influenza virus A, Semliki virus, *Herpes simplex* 1 virus, a marked protective effect is observed when the dipyridamole is administered orally or interperitoneally in single doses 24 hours before, 24 or 72 hours after the viral inoculation.

In its application dipyridamole can be administered either in powder form or granulated (tablets), as aqueous solutions, emulsions or suspensions.

These are the advantages of the proposed interferon induction method:

high interferon titre induction in the organism;

convenient administration technique—the highest interferon titres are achieved in oral administration;

quite low inducer toxicity, relatively high selectivity of the interferon-inducing effect: a characteristic where the dipyridamole markedly exceeds the well-known low-molcular weight inducers as well as practically all high-molecular weight interferon inducers;

relatively continuous preservation of the high interferon levels in the organism—in the serum, even 96 hours after the inducer administration;

clear interferon induction in vitro in cultures both of lymphoid cells (explanted, lines) and in non-lymphoid cells (fibroblasts, etc.); by this characteristics the dipyridamole is superior to most of the well-known low-molecular weight interferon inducers.

This invention is illustrated by the following model embodiment.

Table 1 illustrates data about the dipyridamole interferon-inducing activity in different types of cellular cultures. In mouse peritoneal leucocytes, explanted in vitro, maximum interferon titres are produced under the effect of 100 μM—over 256 IU/ml. This titre is higher than that induced by double-stranded RNA of phague f2 of *E. coli* (5 μg/ml). In monolayer L-cell culture the dipyridamoline in 30 μM concentrations induces over 128 IU/ml which markedly exceeds the interferon production of poly I:C (10 μg/ml).

TABLE 1

Interferon-inducing Dipyridamole Activity in Cellular Cultures

| Cellular Culture | MinIFN-IC micromol/l | OptINF-IC micromol/l | Maximum interferon titre IU/ml |
|---|---|---|---|
| Mouse peritoneal leucocytes | 3 | 100–1000 | ≧256 |
| L-cells | 10 | 30–300 | ≧128 |
| Mouse embryonal fibroblasts | 100 | 300 | 16 |
| Human diploid embryonal fibroblasts | 10 | 100–300 | 16–32 |

TABLE 2

Serum Interferon Level in White Mice after Dipyridamole Intravenous Inoculation

| Dipyridamole dose mg/kg | Interferon Titres (IU/ml) at different time intervals after Dipyridamole Administration | | | | |
|---|---|---|---|---|---|
| hours: | 6th | 12th | 24th | 48th | 72nd |
| 50.0 | | | 8 | 8(4) | |
| 17.7 | | 32 | 16 | | |
| 5.5 | | 16 | 16 | | |
| 1.8 | | 16 | 16 | | 8 |
| 0.6 | <4 | 8 | 32 | 16 | 16 |
| 0.2 | | | ≦4 | 32 | 32 |
| 0.1 | ≦4 | ≦4 | ≦4 | 128 | 32 |
| 0.05 | | | <4 | 64 | 32 |
| 0.01 | | | | | 16 |
| 0 (placebo) | <4 | <4 | <4 | <4 | 4 |

BRIEF DESCRIPTION OF THE DRAWINGS

Table 2 and FIGS. 1 and 2 illustrate the interferon-inducing dipyridamole activity in white mice using different methods of administration: intravenously (Table 2), interperitoneally (FIG. 1) and orally (FIG. 2). In intravenous administration of 0.1 mg/kg the highest titres are reached—relatively late: at the 48th hour (128 IU/ml). The higher doses induce maximum interferon levels at the 12–24th hour.

Figure 1:
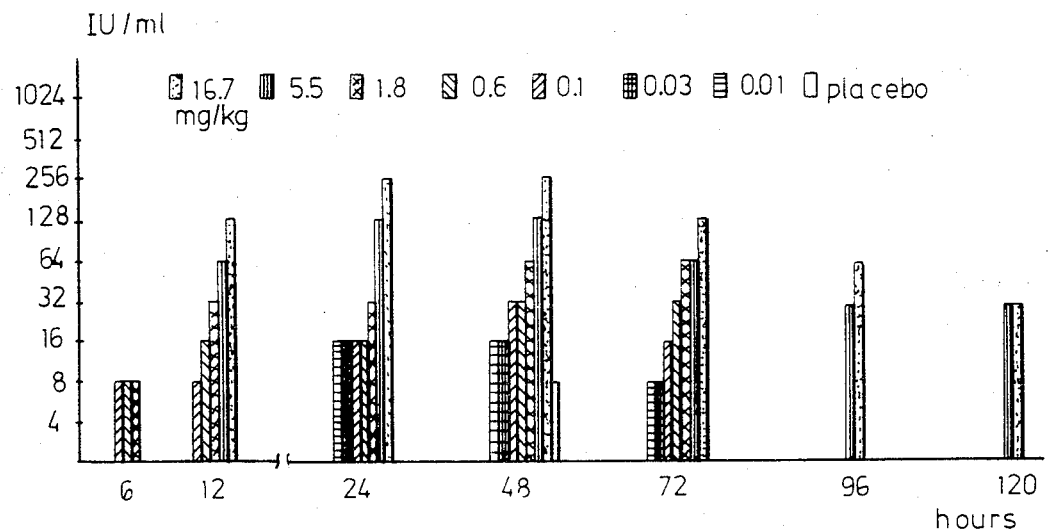
FIG. 1 is a bar graph showing the amount of interferon produced (I.U./ml) in vivo where dipyridamole is administered intraperitoneally to white mice over a period of 120 hours in doses ranging from 0 to 16.7 mg/kg of body weight.

Administered intraperitoneally in a 16.7 mg/kg dose, the dipyridamole induces peak levels of 256 IU/ml in blood on the 24–48th hour after the injection. Marked concentrations are detected until the 120th hour. The lower doses, under 0.1 mg/kg inclusive show lower but better marked activity (FIG. 1)

Figure 2:
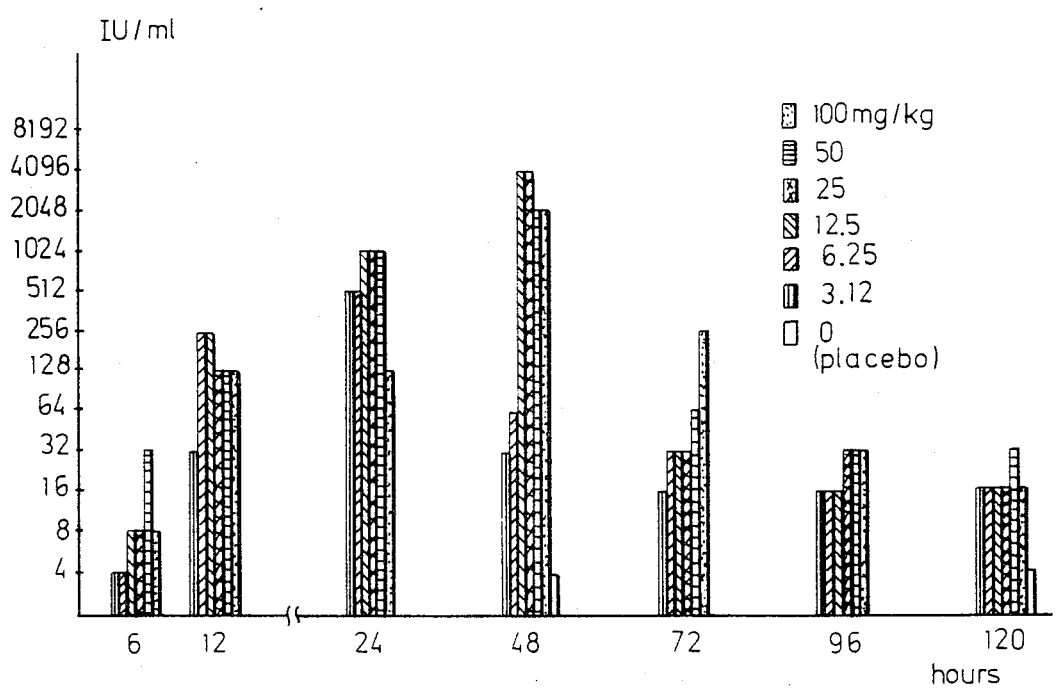
FIG. 2 is a bar graph showing the amount of interferon produced (I.U./ml) in vivo where dipyridamole is administered orally to white mice over a period of 120 hours in doses ranging from 0 to 100 mg/kg of body weight.

Dipyridamole shows maximum interferon-inducing activity in oral administration (FIG. 2); interferon levels in the serum (128–256 IU/ml) are established as early as on the 12th hour under the effect of single doses in the 6.25–100 mg/kg range. Peak values of 4096–8192 IU/ml were reached on the 48th hour after the administration od 12.5 or 25 mg/kg. The interferon titres remain higher than those in the control (placebo) group as long as the 120th hour (FIG. 2).

Table 3 illustrates the dipyridamole interferon-inducing activity in healthy volunteer subjects. Marked raising of the serum interferon level was established in the administration of 100 mg in a single dose orally in a group of 20 men and women aged between 30 and 55 in 80% of them on the 24th and 48th hour.

TABLE 3

Mean Values of Serum Interferon Titres in Human Volunteers Having Positive Response

| Time after dipyridamole administration | Interferon titre IU/ml |
|---|---|
| 0 hours | 5.2 ± 1.7 |
| 24–48 hours | 1069.0 ± 479.7 |

Tables 4 and 5 show some interferon properties induced under the effect of dipyridamole in vitro and in vivo.

TABLE 4

Some Interferon Characteristics Induced Under Dipyridamole Effect

| Titration | Time | Interferon Tyitle (IU/ml/ in: | | |
|---|---|---|---|---|
| | | L-cells | Mouse peritoneal leucocytes | Mouse serum (i.v.) |
| Controls | | 16 | 32 (16) | 128 |
| pH 2.0 | 18 h | 16 | 32 | 128 |
| 56° C. | 30 min | 8 (4) | 16 | 128 |
| | 60 min | 4 | 8 | 8 |
| 65° C. | 30 min | 4 | 8 (16) | 4 |
| 75° C. | 30 min | 4 | <4 | |
| Trypsin | | <4 | <4 | <4 |
| Ether | | 16 (8) | 32 | |
| Ribonuclease | | 16 | 32 | 128 |
| Desoxyribonuclease | | 16 | 32 | 128 |

TABLE 5

Neutralization of Dipyridamole-induced Mouse Interferon by Anti-interferon Serum Globulin

| Interferon preparation | IU in neutralization text mixture | End-point dilution of anti-interferon serum globulin neutralizing interferon activity |
|---|---|---|
| Reference mouse interferon + | 4 | 1:8192 |
| | 2 | 1:16384 |
| | 1 | 1:>65536 |
| Dipyridamole induced mouse interferon ++ | 4 | 1:≧32 |
| | 2 | 1:≧1024 |
| | 1 | 1:≧1024 |

+ induced in cells
++ mouse serum samples intravenously dipyridamole inoculated

Tables 6 and 7 illustrate the dipyridamole level antiviral effect in experimental Semliki virus and *Herpes simplex* 1 virus infections in white mice. The compound was administered in single dose intraperitoneally 24 hours before the viral inoculation. In oral application the effect is much stronger.

TABLE 6

Dipyridamole[(+)] Effect in Semliki Virus Experimental Infection in White Mice (5–10 LD$_{50}$)

| Dipyridamole dose mg/kg | Lethality[(++)] No. | % M ± m | t | Protection coefficient | Protection index % | Activity | Mean survival time:days |
|---|---|---|---|---|---|---|---|
| 1.8 | 3/10 | 30.0 ± 15.27 | 3.02 | 2.4 | 58.0 | ++ | 22.6 ± 3.77 |
| 0.1 | 4/10 | 40.0 ± 16.32 | 2.64 | 1.8 | 44.0 | + | 20.7 ± 3.82 |
| Placebo | 7/10 | 70.0 ± 15.27 | | | | | 12.9 ± 2.91 |

[(+)] Single administration intreperitoneally 24 hours before viral inoculation
[(++)] Traced until the 30th day after infection.

TABLE 7

Dipyridamole Effect[(+)] in Herpes Simplex 1 Virus, Lennett (10 LD$_{50}$) in Experimental Infection

| Dipyridamole dose mg/kg | Lethality[(++)] No. | % M ± m | t | Protection coefficient | Protection index % | activity | Mean survival time days |
|---|---|---|---|---|---|---|---|
| 16–7 | 11/20 | 55.0 ± 11.41 | 3.94 | 1.81 | 44.75 | ++ | 17.3 ± 2.64 |
| Placebo | 19/20 | 95.0 ± 5.0 | | | | | 6.3 ± 1.29 |

[(+)] Single administration intraperitoneally 24 hours before viral inoculation
[(++)] Traced until the 30th day after infection

We claim:

1. A method of treating viral infection responsive to interferon in an animal subject which comprises the step of administering to the animal subject an effective amount of dipyridamole sufficient to induce in vivo production of a pharmaceutically effective amount of the interferon.

2. The method defined in claim 1 wherein the dipyridamole is administered orally, intravenously, or intraperitoneally.

* * * * *